(12) United States Patent
Farina et al.

(10) Patent No.: US 9,708,284 B2
(45) Date of Patent: Jul. 18, 2017

(54) PROCESS FOR THE PREPARATION OF OLOPATADINE AND SYLIL INTERMEDIATES THEREOF

(71) Applicant: LABORATORIO CHIMICO INTERNAZIONALE S.p.A., Milan (IT)

(72) Inventors: Paolo Maria Farina, Casaletto Lodigiano (IT); Renè Ignacio Rodriguez Curiel, Alcantarilla (ES); Stefano Maiorana, Milan (IT); Aldo Bianchi, Solaro (IT); Federica Colombo, Milan (IT); Gabriele Timpano, Garbagnate Milanese (IT)

(73) Assignee: LABORATORIO CHIMICO INTERNAZIONALE S.P.A., Milan (IT)

( * ) Notice: Subject to any disclaimer, the term of this patent is extended or adjusted under 35 U.S.C. 154(b) by 0 days.

(21) Appl. No.: 15/030,711

(22) PCT Filed: Nov. 4, 2014

(86) PCT No.: PCT/IB2014/002331
§ 371 (c)(1),
(2) Date: Apr. 20, 2016

(87) PCT Pub. No.: WO2015/063579
PCT Pub. Date: May 7, 2015

(65) Prior Publication Data
US 2016/0244425 A1    Aug. 25, 2016

(30) Foreign Application Priority Data
Nov. 4, 2013 (IT) .............................. MI2013A1820

(51) Int. Cl.
C07D 313/12    (2006.01)
C07F 7/18      (2006.01)

(52) U.S. Cl.
CPC .......... *C07D 313/12* (2013.01); *C07F 7/1856* (2013.01)

(58) Field of Classification Search
CPC .................................................... C07D 313/12
See application file for complete search history.

(56) References Cited

FOREIGN PATENT DOCUMENTS

| EP | 2 145 882 | 1/2010 |
|----|-----------|--------|
| WO | WO 95/29182 | 11/1995 |
| WO | WO 2007/110761 | 10/2007 |
| WO | WO 2007/119120 | 10/2007 |
| WO | WO 2011/128911 | 10/2011 |

OTHER PUBLICATIONS

International Search Report and Written Opinion of the ISA for PCT/IB2014/002331, mailed Jan. 20, 2015, 11 pages.
Search Report for IT MI20131820, dated Feb. 4, 2014, 3 pages.
International Preliminary Report on Patentability and Written Opinion from PCT with Issuance Date of May 10, 2016 in connection with International Application No. PCT/US2014/002331; 6 pages.

*Primary Examiner* — Noble Jarrell
*Assistant Examiner* — John S Kenyon
(74) *Attorney, Agent, or Firm* — Nixon & Vanderhye P.C.

(57) ABSTRACT

The present invention refers to a new "one-pot" process for the preparation of olopatadine via intermediates of formula (III).

(III)

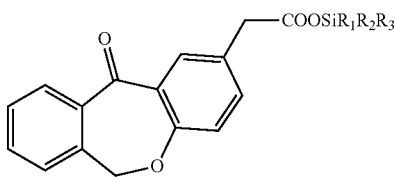

14 Claims, No Drawings

PROCESS FOR THE PREPARATION OF OLOPATADINE AND SYLIL INTERMEDIATES THEREOF

This application is the U.S. national phase of International Application No. PCT/IB2014/002331 filed 4 Nov. 2014, which designated the U.S. and claims priority to IT Patent Application No. MI2013A001820 filed 4 Nov. 2013, the entire contents of each of which are hereby incorporated by reference.

SUMMARY OF THE INVENTION

The present invention refers to a new "one-pot" process for the preparation of olopatadine and salts thereof, and a reaction intermediate.

BACKGROUND OF THE INVENTION

Olopatadine is the international non-proprietary name of {(11Z)-11-[3-(dimethylamino)propylidene]-6,11-dihydrodibenzo[b,e]oxepin-2-yl}acetic acid, having the following formula (I)

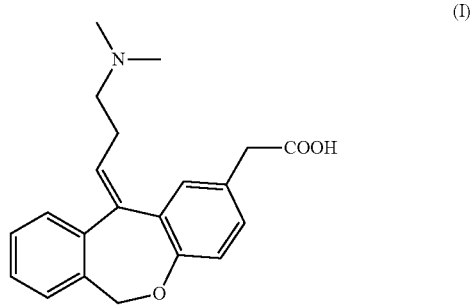 [SMILES: CN(C)CC/C=C1/c2ccccc2COc2ccc(CC(=O)O)cc21]

(I)

and is usually employed as an antihistaminic and is, at present, commercialized to treat eye disorders associated with allergies and allergic conjunctivitis or to treat hives and dermatitis as well.

Several syntheses of olopatadine are known. Such syntheses often comprise a Wittig reaction on the substrate called isoxepac of formula (II)

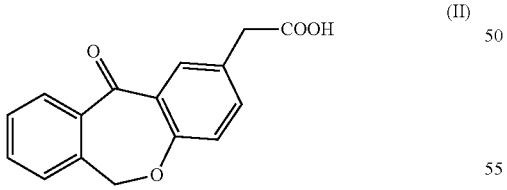

(II)

upon protection with a protecting group forming an ester, and the subsequent cleavage of said protecting group to give the desired compound.

WO2010/007056 discloses the preparation of olopatadine by means of a Wittig reaction carried out on the isoxepac protected by means of esterification with alkyls, cycloalkyls, aryls, aralalkyls or heterocycles or protected in amidic form.

WO2010/121877 discloses the preparation of olopatadine by means of a Wittig reaction carried out on the isoxepac protected by means of esterification with a $C_1$-$C_4$ alkyl.

Such syntheses necessarily require the isolation of the intermediate, i.e. of the protected isoxepac, before carrying out the Wittig reaction and often the isolation of the protected olopatadine as well, before the step of cleaving the protecting group. Such isolations involve laborious recovery operations, the possible purification and drying of said intermediate compounds.

It can be easily understood that, in the framework of the industrial chemical synthesis, each reaction step involving the isolation of an intermediate product has a significant impact on production costs; therefore there is a continuous research on synthesis processes that could be industrially implemented by means of the lowest possible number of reaction steps and without the isolation of the intermediates.

OBJECTS OF THE INVENTION

It is an object of the invention to provide a new process for the preparation of olopatadine and salts thereof which is industrially and economically convenient.

It is a further object of the invention to provide a process for the preparation of olopatadine and salts thereof which is "one-pot", i.e. that does not include the isolation of the intermediate compounds.

It is a further object of the invention to provide a new chemical compound as a reaction intermediate in the synthesis of olopatadine and salts thereof.

DESCRIPTION OF THE INVENTION

It has been now surprisingly found that, protecting the carboxylic group of the compound of formula (II) with a silylating agent to form a silyl-ester derivative of the compound of formula (II), in an aprotic solvent, it is possible to carry out the Wittig reaction, cleave the protecting group and then directly obtain the olopatadine or a salt thereof, in the same reaction mixture, without therefore the need of isolating any intermediate compound.

Thus, according to one of its aspects, it is a subject-matter of the invention a process for the preparation of olopatadine and salts thereof comprising protecting, by means of a silylating agent, the isoxepac compound of formula (II)

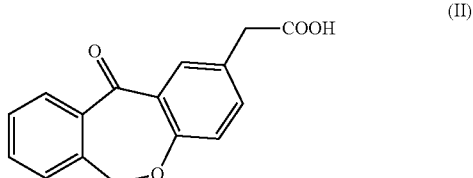

(II)

to give a silyl-ester derivative thereof, of formula (III)

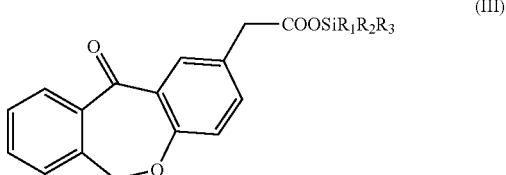

(III)

wherein $R_1$, $R_2$, $R_3$ are selected from alkyl and phenyl, in an aprotic solvent, performing the Wittig reaction in the same reaction solution, cleaving the silylic protecting group (—SiR$_1$R$_2$R$_3$) and isolating olopatadine or a salt thereof, without isolating any intermediate compound.

Pharmaceutically acceptable salts are preferred olopatadine salts, advantageously the hydrochloride salt.

The aprotic solvent has preferably a boiling point above or equal to 50° C., and is advantageously an ether, such as tetrahydrofuran (THF), dioxane, dimethoxyethane or mixtures thereof. THF is a preferred solvent.

The Wittig reaction can be carried out according to the methods well known to one skilled in the art, preferably by employing the 3-dimethylaminopropyltriphenylphosphonium bromide hydrobromide and a strong base, such as, e.g., a hydride, and reacting at a temperature between 50° C. and the boiling point of the reaction mixture, until completion of the reaction.

The reaction mixture is then treated with water to cleave the silyl protecting group and olopatadine (or a salt thereof) is then isolated according to the conventional methods.

According to a preferred embodiment, it is a subject-matter of the invention a process for the preparation of olopatadine and salts thereof comprising
(a) reacting the compound of formula (II')

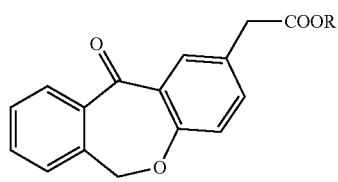

(II')

wherein R represents hydrogen or an alkali metal, with a silylating agent selected from, when R is hydrogen, a N,O-bis(trialkyl-silyl)acetamide, a N,O-bis(alkyl-diphenyl-silyl)acetamide, N,O-bis(triphenyl-silyl)acetamide and hexamethyldisilazane or, when R is an alkali metal, selected from a (trialkyl-silyl)chloride, an (alkyl-diphenyl-silyl)chloride and (triphenyl-silyl)chloride, in an aprotic solvent;
(b) adding 3-dimethylaminopropyltriphenylphosphonium bromide hydrobromide to the reaction mixture from step (a) and subsequently adding a strong base;
(c) adding water into the mixture from step (b) to cleave the silyl protecting group; and
(d) isolating olopatadine and optionally transforming it into a salt thereof.

As it is clear to one skilled in the art, when R is an alkali metal, the compound of formula (II') is isoxepac in salified form. Preferred alkali metals are sodium and potassium, but other isoxepac salts can be used.

According to a preferred embodiment of the invention, R is a hydrogen atom and therefore the compound (II') corresponds to the compound (II), i.e. to the unsalified isoxepac.

The term "alkyl" defines, according to the present invention, a saturated, linear or branched, alkyl derivative having from 1 to 6 carbon atoms, preferably from 1 to 4 carbon atoms, e.g. selected from methyl, ethyl, isopropyl and tert-butyl.

The preferred trialkyl-silyl groups are selected from trimethyl-silyl, triethyl-silyl, dimethylisopropyl-silyl, diethylisopropyl-silyl, tert-butyldimethyl-silyl, triisopropyl-silyl and di-tert-butyl-silyl.

A preferred N,O-bis(trialkyl-silyl)acetamide group is the N,O-bis(trimethyl-silyl)acetamide group.

According to a preferred embodiment of the invention, R is a hydrogen atom and the silylating agent is N,O-bis(trimethyl-silyl)acetamide.

The aprotic solvent used in step (a) is as defined above.

As mentioned, the reaction temperature of step (b) is comprised between 50° C. and the boiling temperature of the reaction mixture, advantageously between 50° C. and 70° C., preferably around 60° C.

The used strong base is preferably a hydride, advantageously sodium hydride, but other strong bases can be used as well.

It has been observed that the amount of 3-dimethylaminopropyltriphenylphosphonium bromide hydrobromide has an effect on the conversion of the compounds of formula (II) and (II') into olopatadine. In particular, it has been noted that molar equivalent ratios between the 3-dimethylaminopropyltriphenylphosphonium bromide hydrobromide and the starting compounds of formula (II) and (II') higher than 2, e.g. comprised between 2 and 4, preferably around 2.5, lead to an almost complete conversion of the starting compound into olopatadine.

The molar equivalent ratios between the starting product (II) or (II')/3-dimethylaminopropyltriphenylphosphonium bromide hydrobromide/strong base, in particular sodium hydride, are preferably around 1/2-4/5-10, advantageously about 1/2.5/8.

The Wittig reaction of step (b) is complete within few hours, e.g. in 2-4 hours. The person skilled in the art can however follow its trend by means of the common chromatographic techniques.

At the end of the reaction, the reaction mixture is preferably quenched, for example by adding a THF/water solution.

In step (c), water is added to the reaction mixture to cleave the silyl group.

Subsequently it is useful, whereas not strictly requested, to extract with organic solvents, e.g. toluene and/or THF and then acidify, in order to remove possible impurities and reaction byproducts before the isolation of the desired compound.

In step (d) olopatadine is isolated, e.g. by extraction with suitable solvents, according to the common processes and, if desired, the so obtained olopatadine can be converted into one of the salts thereof, e.g., according to a preferred embodiment, into the hydrochloride salt thereof.

According to a preferred embodiment, it is a subject-matter of the invention a process for the preparation of olopatadine and salts thereof comprising
e) reacting the isoxepac compound of formula (II)

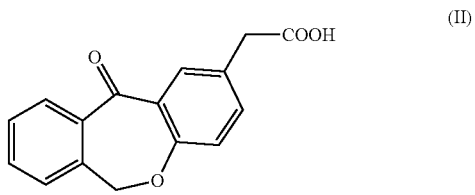

(II)

with N,O-bis(trimethyl-silyl)acetamide in THF, thus forming the intermediate compound of formula (III')

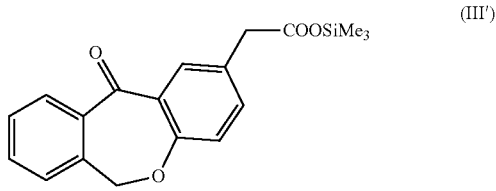

wherein Me represents a methyl group;

f) adding a suspension of 3-dimethylaminopropyltriphenylphosphonium bromide hydrobromide in THF to the reaction mixture from step (e), then adding sodium hydride to the so-formed mixture and allowing it to react, advantageously for about 3 hours at 60° C.;

g) quenching the reaction, e.g. by adding a mixture of THF and water;

h) adding water to cleave the silyl protecting group;

i) isolating the thus obtained olopatadine or transforming it into a salt thereof, for example the hydrochloride salt;

j) optionally, purifying olopatadine or the salt thereof.

The compound (III') corresponds to the compound of formula (III) wherein $R_1$, $R_2$, $R_3$ represent a methyl group.

As mentioned, after the step (h) of cleaving the protecting group, it can be useful, although not strictly requested, to extract with organic solvents, e.g. with toluene and/or THF, then acidify, in order to remove possible impurities and reaction byproducts before the isolation of the desired compound.

The solvent used for the extraction step (i) can be any solvent or mixture of solvents that allow to extract olopatadine; as an illustrative example, THF mixtures or derivatives and alcohols thereof, for example a mixture of 2-methylTHF and 2-propanol, can be used.

An illustrative example of detailed synthesis is provided in the experimental section of the present description.

The intermediate compounds of formula (III) and the intermediate compound of formula (III'), i.e. the trimethylsilyl ester of 6,11-dihydro-11-oxodibenz[b,e]oxepin-2-acetic acid, are new compounds and represent a further subject-matter of the invention. Such compounds are not isolated according to the process of the invention but can be however isolated in order to check the correct development of the reaction or to be used in the preparation of other compounds.

The advantages of the process of the invention with respect to the known art, are clear. The isolation of any intermediate compound and the protection reaction of the carboxylic group are not needed, the Wittig reaction and the subsequent de-protection reaction can all occur in the same reaction mixture, thus eliminating the need of useless processes and reducing in this way the industrial costs of the process. In this way the amount of used solvents is reduced as well.

EXPERIMENTAL SECTION

Example 1

Synthesis of Olopatadine Hydrochloride

At room temperature and under an argon atmosphere, a solution of 6,11-dihydro-11-oxo-dibenz[b,e]oxepin-2-acetic acid (5.0 g, 18.64 mmol, 1 eq) in anhydrous THF (20 ml) was prepared. N,O-bis(trimethyl-silyl)acetamide (4.56 ml, 18.64 mmol, 1 eq) was added and the solution stirred for 1 hour. At room temperature and under an argon atmosphere, a suspension of 3-dimethylaminopropyltriphenylphosphonium bromide hydrobromide (23.7 g, 46.6 mmol, 2.5 eq) in anhydrous THF (80 ml) was prepared. To this suspension the previously prepared solution of trimethylsilyl ester was then added, followed by the sodium hydride (60% in mineral oil, 6.08 g, 152.1 mmol, 7.85 eq). The resulting mixture was heated at 60° C. for 3 hours and the consumption of the starting material was followed by LC-MS. The reaction mixture was cooled to 0° C. and carefully quenched with 40 ml of THF/H$_2$O 1/1 (v/v). After dilution with water (100 ml), the mixture, was washed with toluene (100 ml) and two times with 2-methylTHF (100 ml). The aqueous phase was acidified to pH 1 with 37% hydrochloric acid (8 ml) and then washed with toluene (100 ml). Sodium acetate was added up to pH 5 and the aqueous phase was extracted two times with a mixture of 2-methylTHF/2-propanol 2:1 (v/v) (300 ml). The organic layer was evaporated under reduced pressure. The crude material (8.7 g) was taken up with acetone (90 ml) and acidified with 37% hydrochloric acid, obtaining the precipitation of the cis isomer of olopatadine hydrochloride. The white solid was filtered and washed with acetone. Yield=55%.

The invention claimed is:

1. A process for the preparation of olopatadine of formula (I)

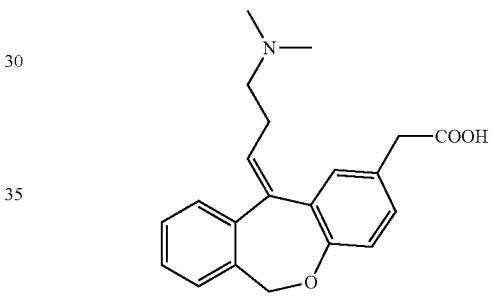

or a salt thereof, comprising protecting, by means of a silylating agent, isoxepac of formula (II)

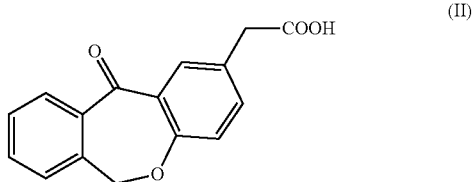

to give a silyl ester derivative thereof of formula (III)

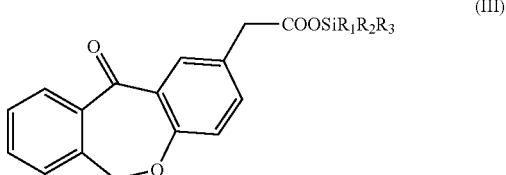

wherein $R_1$, $R_2$, $R_3$ are selected from alkyl and phenyl, in an aprotic solvent; performing the Wittig reaction in the same reaction solution; cleaving the protecting group and obtaining olopatadine or a salt thereof, without isolating any intermediate compound.

2. The process according to claim 1, wherein the Wittig reaction is carried out using 3-dimethylaminopropyltriphenylphosphonium bromide hydrobromide and a strong base.

3. A process for the preparation of olopatadine or a salt thereof, wherein:
(a) reacting the compound of formula (II')

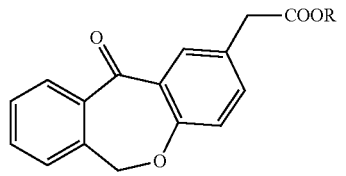

wherein R represents hydrogen or an alkali metal, with a silylating agent selected from, when R is hydrogen, a N,O-bis(trialkyl-silyl)acetamide, a N,O-bis(alkyl-diphenyl-silyl)acetamide, N,O-bis(triphenyl-silyl)acetamide and hexamethyldisilazane or, when R is an alkali metal, a (trialkyl-silyl)chloride, an (alkyl-diphenyl-silyl)chloride and (triphenyl-silyl)chloride, in an aprotic solvent;
(b) adding 3-dimethylaminopropyltriphenylphosphonium bromide hydrobromide to the reaction mixture from step (a) and subsequently adding a strong base;
(c) adding water into the solution from step (b) to cleave the silyl protecting group; and
(d) isolating olopatadine and optionally transforming it into a salt thereof.

4. The process according to claim 1, wherein:
(e) reacting the isoxepac compound of formula (II)

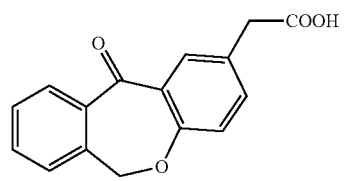

with N,O-bis(trimethyl-silyl)acetamide in THF, thus forming the intermediate compound of formula (III')

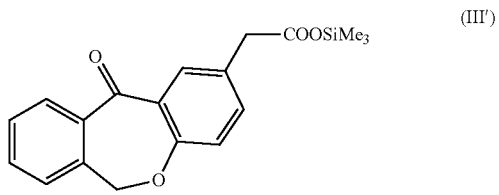

wherein Me represents a methyl group;
(f) adding a suspension of 3-dimethylaminopropyltriphenylphosphonium bromide hydrobromide in THF to the reaction mixture from step (e), then adding sodium hydride to the thus formed mixture and allowing it to react;
(g) quenching the reaction;
(h) adding water;
(i) isolating the thus obtained olopatadine or transforming it into a salt thereof;
(j) optionally purifying the olopatadine or the salt thereof.

5. The process according to claim 1, wherein said aprotic solvent is an ether.

6. The process according to claim 5, wherein said ether is selected from tetrahydrofuran (THF), dioxane, dimethoxyethane and mixtures thereof.

7. The process according to claim 2, wherein said strong base is sodium hydride.

8. The process according to claim 4, wherein in phase (i) hydrochloric acid is added and olopatadine hydrochloride is isolated.

9. The process according to claim 3, wherein R is a hydrogen atom and said silylating agent is N,O-bis(trimethyl-silyl)acetamide.

10. The process according to claim 4 wherein in step (i) a solvent mixture of 2-methyl-THF and 2-propanol is used to extract and isolate olopatadine.

11. The process according to claim 2, wherein the ratio between compound (II)/3 dimethylaminopropyltriphenylphosphonium bromide hydrobromide/strong base is about 1/2.5/8.

12. The process according to claim 3, wherein, after the protecting group cleaving step (c), an extraction with organic solvents is performed, and then acid is added to remove the possible impurities and reaction byproducts.

13. The process according to claim 3, wherein the ratio between compound (II')/3-dimethylaminopropyltriphenylphosphonium bromide hydrobromide/strong base is about 1/2.5/8.

14. The process according to claim 4, wherein, after step (h), an extraction with organic solvents is performed, and then acid is added to remove the possible impurities and reaction byproducts.

* * * * *